United States Patent
Thompsen et al.

(10) Patent No.: US 10,114,001 B2
(45) Date of Patent: Oct. 30, 2018

(54) QUANTITATION OF AMINES IN HYDROCARBONS

(71) Applicant: PHILLIPS 66 COMPANY, Houston, TX (US)

(72) Inventors: Jim C. Thompsen, Bartlesville, OK (US); Johnnie M. Parnell, Jr., Bartlesville, OK (US)

(73) Assignee: Phillips 66 Company, Houston, TX (US)

( * ) Notice: Subject to any disclaimer, the term of this patent is extended or adjusted under 35 U.S.C. 154(b) by 621 days.

(21) Appl. No.: 14/817,944

(22) Filed: Aug. 4, 2015

(65) Prior Publication Data

US 2016/0033459 A1    Feb. 4, 2016

Related U.S. Application Data

(60) Provisional application No. 62/032,857, filed on Aug. 4, 2014.

(51) Int. Cl.
*G01N 33/28*    (2006.01)
*G01N 30/88*    (2006.01)

(52) U.S. Cl.
CPC .   *G01N 33/2835* (2013.01); *G01N 2030/8818* (2013.01)

(58) Field of Classification Search
CPC ................................................ G01N 33/2835
See application file for complete search history.

(56) References Cited

U.S. PATENT DOCUMENTS

| | | | | | |
|---|---|---|---|---|---|
| 4,125,373 | A | * | 1/1978 | Scoggins | 47/397 |
| 4,289,812 | A | * | 9/1981 | Martin | 47/397 |
| 4,474,885 | A | * | 10/1984 | Maki | 47/397 |
| 5,151,177 | A | * | 10/1992 | Buck et al. | 47/397 |

\* cited by examiner

*Primary Examiner* — Lisa Caputo
*Assistant Examiner* — Alex Devito
(74) *Attorney, Agent, or Firm* — Phillips 66 Company

(57) ABSTRACT

The present disclosure relates to methods for quantitation of amines in hydrocarbon stream. More specifically, the disclosure relates to rapid, precise and highly-sensitive methods for quantitating hydrogen sulfide-scavenging amines in crude petroleum oil or refinery streams.

15 Claims, 3 Drawing Sheets

QUANTITATION OF AMINES IN HYDROCARBONS

CROSS-REFERENCE TO RELATED APPLICATIONS

This application is a non-provisional application which claims the benefit of and priority to U.S. Provisional Application Ser. No. 62/032,857 filed Aug. 4, 2014, titled "Quantitation of Amines in Hydrocarbons," which is hereby incorporated by reference in its entirety.

STATEMENT REGARDING FEDERALLY SPONSORED RESEARCH OR DEVELOPMENT

None.

FIELD OF THE INVENTION

The present disclosure relates to methods for quantitation of amines in hydrocarbon stream. More specifically, the disclosure relates to rapid, precise and highly-sensitive methods for quantitating hydrogen sulfide-scavenging amines in crude petroleum oil or refinery streams.

BACKGROUND

Crude petroleum oils often contain or generate hydrogen sulfide ($H_2S$) during handling, storage and transportation, which can be corrosive and/or lethal to workers. Thus, $H_2S$ scavengers (e.g., triazine compounds) are frequently added to crude oil to suppress $H_2S$ evolution during transport to avoid exposure of personnel involved with overland or waterborne shipping. Most commercial $H_2S$ scavengers are based on amines, including ethanolamines. Unfortunately, these amines can be extremely corrosive to refinery equipment. During desalting and subsequent atmospheric crude oil distillation, these amines can act as chloride ion transporters which are active corrosion agents in the distillation tower trays, top pump around (TPA) exchangers, the overhead vapor line and condensers. Corrosion rates of 2000 to 5000 mpy in naptha draw line and distillation tower trays have been commonly observed.

Quantitating the molecular species and concentrations of these H2S scavenging amines is important to refiners because even low ppm levels of certain amine species can significantly affect the behavior of the crude oil in desalting and atmospheric distillation units. Significant concentration of amines present in the oil can occur during refining, such that an amine level in the low ppm (or even sub-ppm) range can result in an amine level exceeding 100 ppm in the overhead water stream of a refinery atmospheric distillation tower.

Current methods lack proper sensitivity to detect amines, are too labor intensive and take too long to complete, often causing delays in the refining of a given batch of crude oil. Thus, it is essential to develop an accurate and precise method for rapidly (<6 hours) identifying and quantitating amine species in crude oil samples at levels less than 10 ppm.

BRIEF SUMMARY OF THE DISCLOSURE

Certain embodiments of the invention comprise a process for quantitation of amines in a crude petroleum oil, including warming a crude oil sample to a temperature of between 20° C. and 150° C.; adding water and a solvent to the sample to create an extraction mixture, where the water is added at a ratio ranging from about 1:10 to about 10:1 (by volume), and where the solvent is added at a ratio ranging from about 1:10 to about 10:1 (by volume). The extraction mixture is then heated at a temperature ranging from 50° C. to 160° C., for a period of time ranging from 5 minutes to 5 hours to produce an extracted amine mixture that includes an oil phase and an aqueous phase; analyzing at least a portion of the aqueous phase by ion chromatography for quantitation of amines. In certain embodiments, the crude petroleum oil sample is sonicated while warming, to increase homogeneity of the sample, and the heating is optionally microwave heating.

The heating is optionally conducted at a target temperature ranging from 80° C. to 140° C., or in certain embodiments, ranging from 100° C. to 130° C. Optionally, the heating of the extraction mixture may be performed multiple times, mixing the extraction mixture between each heating. Each heating cycle can be performed for a period of time ranging from 20 minutes to 2 hours. During the heating, the temperature of the extraction mixture may be increased to the target temperature over a period ranging from 2-30 minutes, optionally, 10-30 minutes. In certain embodiments, the pH is kept in a range of between 1 and about 6.

The process can consistently detect the presence of hydrogen sulfide scavenging amines, or their hydrolysis products at a level of less than 1 ppm, or even less than 0.5 ppm.

BRIEF DESCRIPTION OF THE DRAWINGS

A more complete understanding of the present invention and benefits thereof may be acquired by referring to the follow description taken in conjunction with the accompanying drawings in which.

Figure 1:
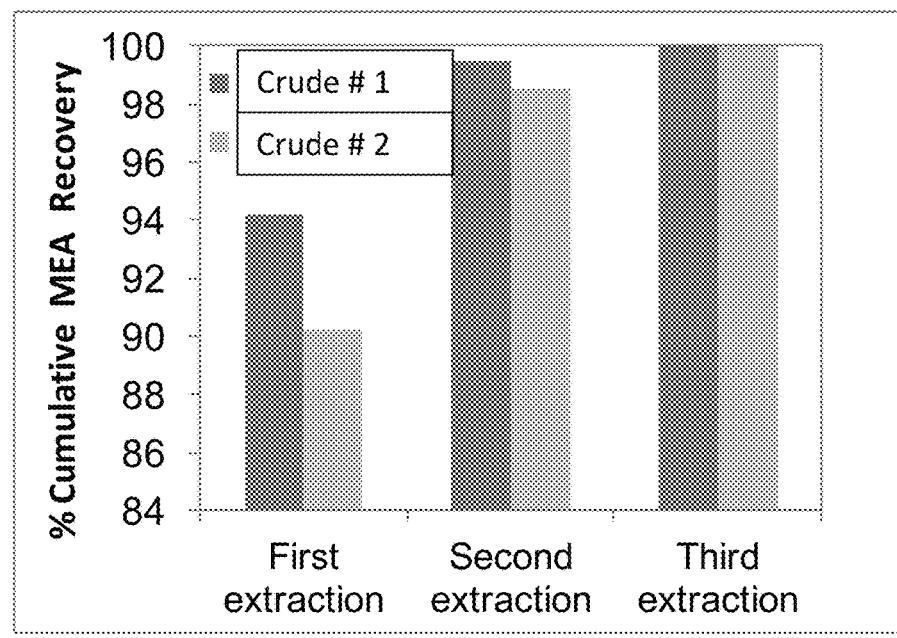
FIG. 1 is a bar graph representing an exemplary embodiment, showing cumulative percent recovery of an amine from a crude oil sample by repeated extraction using the processes detailed herein.

The invention is susceptible to various modifications and alternative forms, specific embodiments thereof are shown by way of example in the drawings. The drawings may not be to scale. It should be understood that the drawings and their accompanying detailed descriptions are not intended to limit the scope of the invention to the particular form disclosed, but rather, the intention is to cover all modifications, equivalents and alternatives falling within the spirit and scope of the present invention as defined by the appended claims.

DETAILED DESCRIPTION

Triazine is a generic term for chemicals that contain a six member heterocyclic ring with three nitrogen and three carbon atoms. Triazine compounds differ in the atoms or functional groups bound exclusively to nitrogen. One commonly-used triazine compound is Hexahydro-1,3,5-tris(2-hydroxyethyl)-triazine (HTZ). Equation 1 shows that the reaction of HTZ with $H_2S$ proceeds by the successive substitution of the ring nitrogen atoms with sulfur at a decreasing reaction rate, displacing the nitrogen and attached group via a nucleophilic substitution. The stability and solubility (in oil) of the intermediates follow the order 4 (if formed—not kinetically favored)>3>2>1 (if remaining). Additionally, as shown in Equation 1, three moles of monoethanolamine are formed for each three moles of H2S scavenged by reaction with HTZ.

Equation 1:

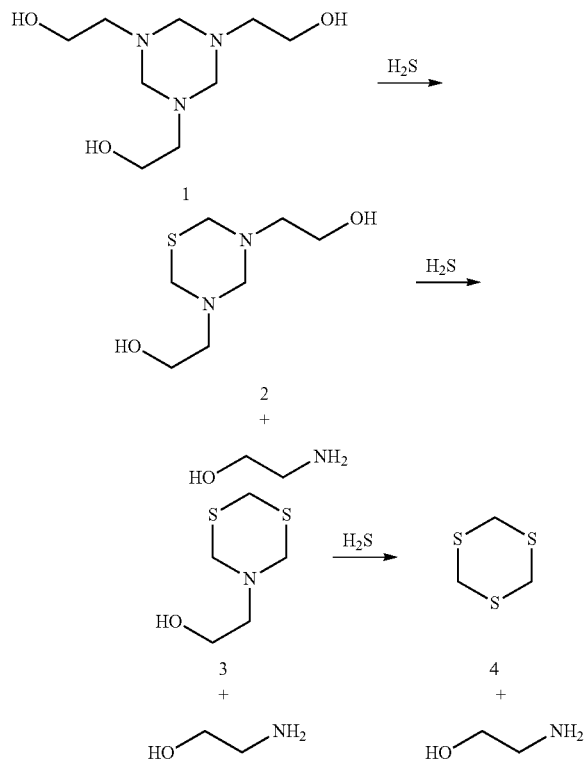

A competing side reaction is the hydrolysis of the triazine molecule (Equation 2). Additionally, triazines may undergo thermal degradation. Both reactions generate MEA.

Equation 2:

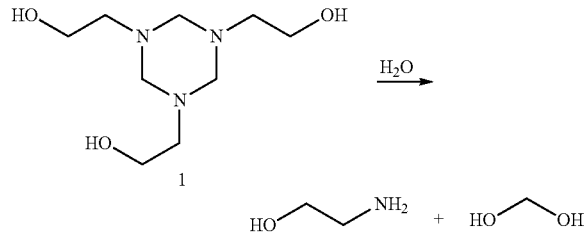

The present method enables separate quantitation of several different amines, including monoethanolamine (MEA), diethanolamine (DEA), methyldiethanolamine (MDEA), and dimethylethanolamine (DMEA). The process additionally does not cause significant degradation of the amines MEA, DEA, MDEA, and DMEA, which increases its accuracy.

MEA is highly water-soluble, but amine intermediates 1 (if formed), 2 and 3 shown in Equation 1 have varying solubility in water. Unlike prior methods, the process disclosed herein effectively extracts a large percentage of these $H_2S$ scavenging amines in a crude oil sample with a single extraction.

Certain embodiments comprise a process for quantitation of amines in a crude petroleum oil or in a partially-refined hydrocarbon stream. The crude petroleum oil (or partly-refined hydrocarbons) is first warmed to a temperature of between 20° C. and 150° C. Without wishing to be bound by theory, this is believed to assist in homogenizing the oil or hydrocarbons. Once warmed, the oil/hydrocarbons is mixed by hand or utilizing a conventional power vortexer. A sample is taken for extraction.

Extraction is begun by adding an amount of water to the sample at a ratio ranging from about 1:10 to about 10:1 (v/w). In certain embodiments, the water is added at approximately a 1:1 ratio (v/w) to the sample. A solvent is optionally added to the sample that is at least partly soluble in the oil or hydrocarbon sample, and immiscible with the water phase. In certain embodiments, this solvent may comprise xylene, toluene, heptane, hexane or any other solvent (or combination of solvents) that is miscible with the oil sample and capable of both reducing the viscosity of the oil phase and increasing surface area contact between the oil and water phases. The solvent is added to the at a ratio ranging from about 1:10 to about 10:1 (v/v), and order of addition to the sample (before or after water) is not important. In certain embodiments, the solvent is added at approximately a 1:1 ratio (v/v). Although not wishing to be bound by theory, it is hypothesized that the presence of the solvent acts to enhance the extraction of amines by decreasing the viscosity of the hydrocarbon sample, while increasing interaction of the hydrocarbons and the water.

The extraction mixture is then heated to a target temperature ranging from 50° C. to 160° C., for a period of time ranging from 5 minutes to 5 hours to produce an extracted amine mixture that includes a non-polar oil phase and a polar phase containing extracted amines. In certain embodiments, the heating is optionally provided by microwaves, although any conventional heating device capable of holding a relatively constant temperature may be suitable for the process. In certain embodiments, the target temperature ranges from 80° C. to 140° C., or even from 100° C. to 130° C.

Optionally, the heating of the extraction mixture may be performed in multiple heating cycles. Optionally the extraction mixture may be mixed between each heating cycle to increase mixing of refluxed aqueous phase with the oil phase on the interior of the heating vessel. Each heating cycle can be performed for a period of time ranging from 20 minutes to 2 hours. During the heating, the temperature of the extraction mixture may be increased to the target temperature over a period ranging from 2-30 minutes, optionally, 10-30 minutes.

In certain embodiments, the pH of the extraction mixture is maintained in a range of between 1 and about 6. We have found that partitioning of amines to the oil phase in an oil:water extraction correlates directly with increasing pH. Although not wishing to be bound by theory, it is hypothesized that an acidic pH decreases solubility of the target amines in the non-polar oil phase, consequently increasing their extraction into the aqueous phase. Thus, in certain embodiments, the extraction of amines may be conducted in an acidic environment. This can be accomplished using any of a number of conventional acids to decrease the pH of the extraction water to between 1 and 6, and thus, will not be discussed further.

Following the heating of the extraction mixture, at least a portion of the water is optionally filtered in preparation for analysis of amine content by ion chromatography. Generally, filtration through a 0.45 micron syringe filter rated for IC analysis is sufficient. A portion of the filtrate is analyzed by ion chromatography using conditions that allow resolution of various amines on an ion chromatogram as they elute from the chromatography column. In certain embodiments, a conventional reverse-phase column may be used, as is understood by one having skill in the art.

Amines may be eluted from the chromatography column by any known solvent or combination of solvents utilized at a constant concentration or a concentration gradient that allows proper resolution of various amine species as they elute from the chromatography column. In certain embodiments, elution is achieved using a gradient of methanesulfonic acid (MSA) ranging from 1 mM to 30 mM.

The microwave extraction method provides better recovery of amines as it promotes vigorous mixing (boiling) of the water and oil phases when held at 120° C. Despite this refluxing for an extended period of time, Table 1 shows that no appreciable degradation of analyzed amines was observed when standards containing known amounts of amines were subjected to four heat cycles of 90 minutes each at 120° C.

TABLE 1

Analysis of Amine Standards Subjected to Refluxing at 120° C. (4 × 90 min)

| Sample (10 ppm) | MEA | DEA | MDEA | DMEA | Mixed Std. |
|---|---|---|---|---|---|
| | | | Detected (ppm) | | |
| MEA | 10.7 | * | * | * | 9.3 |
| MMA | * | * | * | * | * |
| DEA | * | * | * | * | 9.5 |
| DMA | * | * | 0.1 | 0.1 | 0.2 |
| MDEA | * | * | 9.4 | * | 8.6 |
| DMEA | * | * | * | 9.0 | 10.7 |
| TMA | * | * | * | * | * |
| Ammonium | * | * | * | * | * |

The processes described herein are designed to consistently extract a high percentage of the amines present in the oil in a single extraction. Referring to FIG. 1, the inventive process was observed to extract approximately 94 wt. % and 90.8 wt. %, respectively, of MEA from two crude samples having different API values. A second extraction increased the cumulative percentage of extracted MEA to 99.5% and 98.5%, respectively (shown in FIG. 1), but is not required for accurate quantitation of amine species and quantity.

The process described herein has a number of advantages over previous methods, including, but not limited to, high-sensitivity enabling quantitative determination of monoethanolamine in crude oil down to 0.1 ppm (w/w). The process can consistently detect the presence of hydrogen sulfide scavenging amines, or their hydrolysis products at a level of less than 1 ppm, or even less than 0.5 ppm.

We compared the present method to a previously utilized method for extracting amines from crude oil samples. Briefly, the prior process involved extracting amines from the oil into acidic water (pH 1) with vortexing at room temperature. Table 2 compares the levels of various amines detected in five different crude oil samples using the present methods comprising microwave heating extraction (MWE) versus the prior acid-extraction (AE) methodology.

TABLE 2

Comparing Amine Detection Sensitivity of Microwave Heating Extraction (MWE) Versus Acid Extraction (AE).

| | Crude | | | | | | | | | |
|---|---|---|---|---|---|---|---|---|---|---|
| | 1 | | 2 | | 3 | | 4 | | 5 | |
| | | | | | Method | | | | | |
| Amine | MWE | AE | MWE | AE | MWE | AE | MWE | AE | MWE | AE |
| MEA | 2.1 | 0.6 | 4.0 | 0.4 | 6.1 | 1.0 | * | * | * | * |
| DEA | * | * | * | * | * | * | * | * | * | * |
| MDEA | * | * | * | * | * | * | * | * | * | * |
| DMEA | * | * | * | * | * | * | 3.0 | 0.1 | 10.6 | 1.9 |

(* = below 0.1 ppm)

Figure 2:
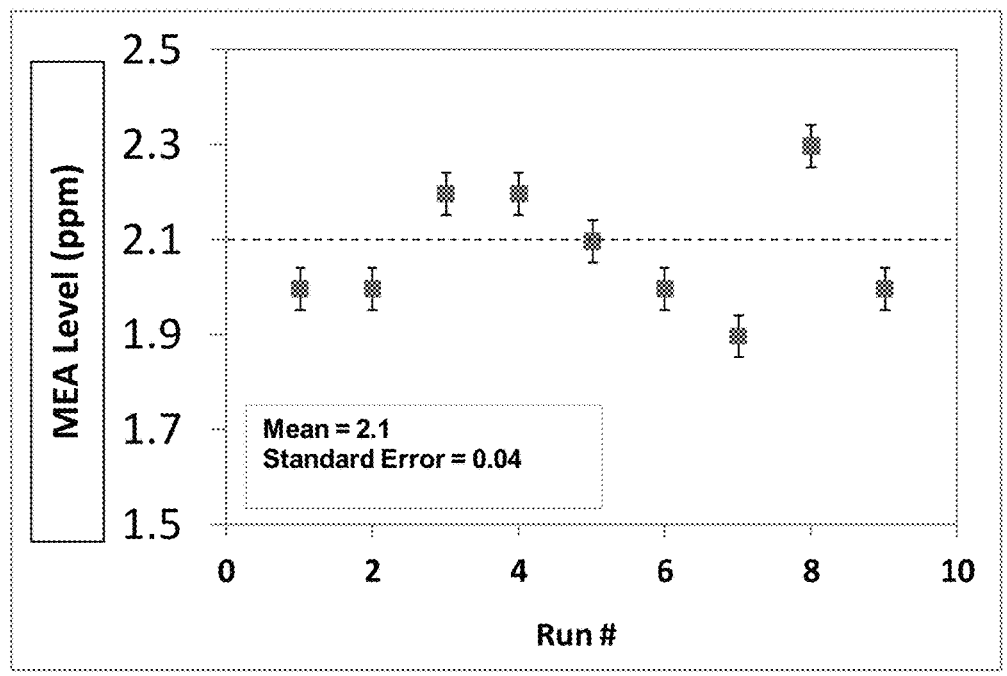
FIG. 2 is a graph showing the relative precision of an exemplary embodiment of the present disclosure.

The present inventive methods are also precise. FIG. 2 demonstrates that repeated analysis of a sample using the methods of the present disclosure resulted in an average detected MEA value of 2.1 ppm, with a Standard Error of the Mean=0.04 ppm.

Despite being a highly sensitive and precise assay, necessity requires that a useful amine analysis assay be capable of rapidly processing a large number of samples (at least 20) in order to be practical for solving refinery processing problems (e.g., determining whether a given crude oil feed contains amines). The present method minimizes the extraction cycles required, and the overall extraction time required, which greatly reduces the total time needed for amine quantitation. The methods disclosed herein extract >90% of amines from a crude oil sample in a single extraction, saving time and limiting required handling time by the technician. A large number of samples (at least 20) can be extracted over a period of about 6 hours (i.e. four heating cycles) utilizing a single microwave oven, which is a much greater throughput than prior methods.

The following examples are intended to be illustrative of specific embodiments in order to teach one of ordinary skill in the art how to make and use the invention These examples are not intended to limit the scope of the invention to the disclosed embodiments. Rather, the intention is to cover all modifications, equivalents and alternatives falling within the spirit and scope of the present invention as defined by the appended claims and supported by the complete disclosure.

Example 1

An oil sample was heated to about 50° C. in a heating sonicator. The sample was shaken with a vortex mixer for one minute and 10 grams was transferred into a microwavable vessel. To the sample was added 9 ml of ultrapure water and 9 ml of xylene solvent. Each mixture was briefly hand-mixed and inserted into a rack inside a programmable temperature microwave oven (Mars 6 Microwave, CEM Corporation).

The microwave was set to ramp temperature from 20° C. to 120° C. in 20 minutes and hold at 120° C. for 60 min. This heating cycle was repeated three additional times. After the cycles 1-3, each vessel was rolled on its side to gather the refluxed water droplets on the vessel walls. Following the fourth heat cycle, the vessels were left upright so as to not disturb the phase separation.

The bottom aqueous phase was removed from each vessel, and filtered through a 0.45 micron syringe filter rated for IC analysis. A portion of the filtrate was analyzed by ion chromatography on a Dionex Model ICS5000 ion chromatography system (Thermo-Fisher Scientific) using the following conditions: Sample Injection Volume: 25 uL; Columns: CG19-2 mm P/N 076029 and CS19-2 mm separating column at 30° C.; Suppressor: CSRS300-2 mm with a Regenerant at 12 mA in Recycle Mode.

Amines were eluted from the column with methanesulfonic acid (MSA) according to the following eluent gradient: 1 mM (MSA) at −6 minutes, 1 mM MSA at 0 minutes, 1 mM MSA at 2 minutes, 5 mM MSA at 22 minutes, 15 mM MSA at 35 minutes, 20 mM MSA at 35.1 minutes, and 20 mM MSA at 65 minutes. Flow Rate: 0.25 ml/min. Run Time: 65 minutes. Calibration curves for amines are nonlinear, particularly under 50 ppm, and so were prepared using 8 to 10 concentrations of amine standard with a fixed mode, point-to-point, normal-curve fit.

Figure 3:
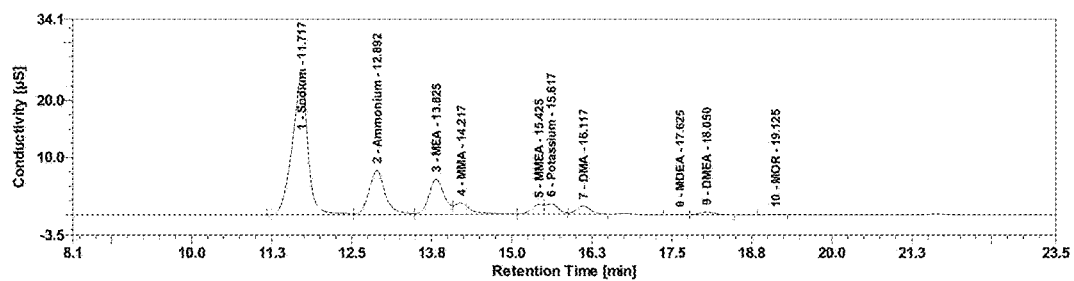
FIG. 3 is a ion chromatogram of an embodiment of the present disclosure showing the distribution of amines eluted from a chromatography column.

A representative chromatogram of the eluted amines is shown in FIG. 3. Quantitation of each amine in the sample was performed by integration of the area under the peak relative to peak areas along the calibration curve.

In closing, it should be noted that the discussion of any reference is not an admission that it is prior art to the present disclosure, in particular, any reference that may have a publication date after the priority date of this application. At the same time, each and every claim below is hereby incorporated into this detailed description or specification as a additional embodiments of the present invention.

Although the systems and processes described herein have been described in detail, it should be understood that various changes, substitutions, and alterations can be made without departing from the spirit and scope of the invention as defined by the following claims. Those skilled in the art may be able to study the preferred embodiments and identify other ways to practice the invention that are not exactly as described herein. Thus, the invention disclosed herein is specifically intended to be as broad as the claims below and those variations and equivalents that are encompassed by the scope of the claims. The abstract and drawings are not intended to limit the scope of the invention.

We claim:

1. A process for quantitation of amines in a petroleum oil, comprising:
   (a) warming a petroleum oil sample to a temperature of 20° C. to 150° C.;
   (b) adding water and a solvent to the petroleum oil sample to create an extraction mixture;
   (c) heating the extraction mixture to a temperature ranging from 50° C. to 160° C., and maintaining at a constant the temperature for a period of time ranging from 5 minutes to 5 hours to produce an extracted amine mixture comprising an oil phase and an aqueous phase;
   (d) analyzing at least a portion of the aqueous phase by ion chromatography for quantitation of amines.

2. The process of claim 1, wherein during the warming, the petroleum oil sample is sonicated to increase homogeneity.

3. The process of claim 1, wherein the heating is supplied by microwaves.

4. The process of claim 1, wherein the solvent is at least partially soluble in the petroleum oil sample, but immiscible with the water.

5. The process of claim 1, wherein the solvent reduces the viscosity of the oil phase and increases surface area contact between the oil and aqueous phases.

6. The process of claim 1, wherein during the extraction, the pH is kept in a range of between 1 and about 6 to increase solubility of the amines in the aqueous phase.

7. The process of claim 1, wherein the heating is conducted for a period of time ranging from 20 minutes to 2 hours.

8. The process of claim 1, wherein the heating of the extraction mixture is performed multiple times.

9. The process of claim 1, wherein the heating comprises heating the extraction mixture to a temperature ranging from 80° C. to 140° C.

10. The process of claim 1, wherein the heating comprises heating the extraction mixture to a temperature ranging from 100° C. to 130° C.

11. The process of claim 1, wherein the heating comprises increasing the temperature of the extraction mixture over a period ranging from 2 to 30 minutes to the temperature ranging from 50° C. and 160° C., then maintaining that temperature.

12. The process of claim 1, wherein the heating comprises increasing the temperature of the extraction mixture over a period ranging from 10 to 30 minutes to the temperature ranging from 50° C. and 160° C., then maintaining that temperature.

13. The process of claim 1, wherein the analyzing by ion chromatography is in part conducted by eluting the amines with an increasing gradient of methane sulfonic acid to resolve individual amine species.

14. The process of claim 1, wherein the process consistently detects the presence of hydrogen sulfide scavenging amines, or their hydrolysis products at a level of less than 1 ppm.

15. The process of claim 1, wherein the process consistently detects the presence of hydrogen sulfide scavenging amines, or their hydrolysis products at a level of less than 0.5 ppm.

* * * * *